US012661406B2

(12) United States Patent
Li et al.

(10) Patent No.: US 12,661,406 B2
(45) Date of Patent: Jun. 23, 2026

(54) FILM-FORMING COMPOSITION CONTAINING GELLAN GUM AND STARCH, AND APPLICATION IN SOFT CAPSULE

(71) Applicant: SIRIO PHARMA CO., LTD., Shantou (CN)

(72) Inventors: Xufa Li, Shantou (CN); Qiong Chen, Shantou (CN); Suqiong Fang, Shantou (CN); Xuteng Yang, Shantou (CN)

(73) Assignee: SIRIO PHARMA CO., LTD., Shantou (CN)

( * ) Notice: Subject to any disclaimer, the term of this patent is extended or adjusted under 35 U.S.C. 154(b) by 0 days.

(21) Appl. No.: 17/614,644

(22) PCT Filed: Dec. 28, 2020

(86) PCT No.: PCT/CN2020/140148
§ 371 (c)(1),
(2) Date: Nov. 29, 2021

(87) PCT Pub. No.: WO2021/136169
PCT Pub. Date: Jul. 8, 2021

(65) Prior Publication Data
US 2022/0226478 A1    Jul. 21, 2022

(30) Foreign Application Priority Data

Dec. 30, 2019    (CN) .......................... 201911394755.3

(51) Int. Cl.
| | |
|---|---|
| A61K 47/36 | (2006.01) |
| A23L 29/269 | (2016.01) |
| A23L 29/30 | (2016.01) |
| A23P 10/30 | (2016.01) |
| A61K 9/48 | (2006.01) |

(52) U.S. Cl.
CPC ............. A61K 47/36 (2013.01); A23L 29/272 (2016.08); A23L 29/30 (2016.08); A23P 10/30 (2016.08); A61K 9/4816 (2013.01)

(58) Field of Classification Search
CPC ....... A61K 47/36; A61K 9/4816; A23L 29/30; A23L 29/272; A23P 10/30
See application file for complete search history.

(56) References Cited

U.S. PATENT DOCUMENTS

| | | | | |
|---|---|---|---|---|
| 4,874,756 | A | 10/1989 | Mertens | |
| 6,602,996 | B1 | 8/2003 | Sworn | |
| 8,231,921 | B2 | 7/2012 | Bezanson | |
| 8,765,167 | B2 | 7/2014 | Myers | |
| 9,107,432 | B2 | 8/2015 | Muller | |
| 11,847,726 | B2 | 12/2023 | Sima | |
| 2005/0196436 | A1* | 9/2005 | Chantranukul | ...... A61K 9/4816 426/573 |
| 2007/0034827 | A1 | 2/2007 | Li | |

| | | | | |
|---|---|---|---|---|
| 2010/0240724 | A1* | 9/2010 | Chang | ...................... A61P 1/00 514/774 |
| 2011/0319503 | A1 | 12/2011 | Muller | |
| 2013/0302309 | A1 | 11/2013 | Yang | |
| 2016/0136101 | A1 | 5/2016 | Sydow | |
| 2016/0151243 | A1 | 6/2016 | Sydow | |
| 2017/0172931 | A1* | 6/2017 | Kim | ..................... A61K 9/4816 |
| 2017/0224707 | A1 | 8/2017 | Kuusisto | |
| 2019/0117781 | A1 | 4/2019 | Tian | |
| 2020/0017609 | A1 | 1/2020 | Yuan | |
| 2021/0128481 | A1 | 5/2021 | Zhang | |
| 2021/0196641 | A1 | 7/2021 | Obatake | |

FOREIGN PATENT DOCUMENTS

| | | |
|---|---|---|
| CN | 1663989 A | 9/2005 |
| CN | 1995115 A | 7/2007 |
| CN | 101406704 A | 4/2009 |
| CN | 100510052468 C | 8/2009 |
| CN | 102365159 A | 12/2011 |
| CN | 104721167 A | 6/2015 |
| CN | 104873977 A | 9/2015 |
| CN | 105263462 A | 1/2016 |
| CN | 106456558 A | 2/2017 |

(Continued)

OTHER PUBLICATIONS

Morrison NA et al: "Gelatin alternatives for the food industry", Physical Chemistry and Industrial Application of Gellan Gum : [ . . . Presented at the Osaka City University International Symposium '98—Joint Meeting With the 4th International Conference on Hydrocolloids (OCUIS98—4ICH) in Oct. 1998], Springer, DE, vol. 114, Dec. 31, 1999 (Dec. 31, 1999), pp. 127-131.
European Search Report for European Patent Application No. 20909141.2 dated Dec. 15, 2022, 6 pages.
International Search Report and Written Opinion of International Application No. PCT/CN2020/140148 mailed Mar. 26, 2021, 13 pgs.
Chen Fengfeng et al. Rice starch granule/chitosan composite preparation of microcapsules Applied Chemical Industry vol. 45 Oct. 2016.
Qiang Minghui et al. Development of glue viscosity control system based on capsule shell production line Automation and Instrumentation Issue 8, 2015.

(Continued)

*Primary Examiner* — Doan T Phan
(74) *Attorney, Agent, or Firm* — Lowenstein Sandler LLP

(57) ABSTRACT

Provided is a starch film-forming composition, comprising: A, a first gelling agent; B, starch; C, a plasticizer; D, water; wherein the first gelling agent is a gellan gum with two gel temperatures, wherein the first gel temperature is 51 to 75° C. and the second gel temperature is 40° C. to 50° C. The present application relates to the field of food or pharmaceutical raw materials. The composition is obviously superior to the prior art in terms of rubber strength, toughness and forming bonding when used in preparation of soft capsules, can fully meet the requirements for industrial production of soft capsules and can be used as an alternative in soft capsule technology.

14 Claims, No Drawings

(56) References Cited

FOREIGN PATENT DOCUMENTS

| CN | 108659137 | A | 10/2019 |
|----|-----------|---|---------|
| CN | 11044455 | A | 11/2019 |
| CN | 112494453 | A | 3/2021 |
| CN | 113121889 | A | 7/2021 |
| CN | 113332257 | A | 9/2021 |
| CN | 113398088 | A | 9/2021 |
| CN | 113592985 | A | 11/2021 |
| CN | 113768137 | A | 12/2021 |
| EP | 1792939 | A1 | 11/2006 |
| EP | 1570843 | B1 | 9/2011 |
| EP | 2 815 745 | A1 | 12/2014 |
| EP | 2815744 | A1 | 12/2014 |
| EP | 3010493 | A1 | 4/2016 |
| EP | 3735707 | A1 | 11/2020 |
| EP | 4134072 | A1 | 2/2023 |
| JP | 2002517568 | A | 6/2002 |
| JP | 2005281687 | A | 10/2005 |
| JP | 2007153851 | A | 6/2007 |
| JP | 2007153889 | A | 6/2007 |
| JP | 2009040716 | A | 2/2009 |
| JP | 2016199737 | A | 12/2016 |
| JP | 20188886 | | 8/2019 |
| TW | 201944985 | A | 12/2019 |
| WO | 0031146 | A1 | 6/2000 |
| WO | 2009123257 | A1 | 10/2009 |
| WO | 2014202754 | A1 | 12/2014 |
| WO | 2014202757 | A1 | 12/2014 |
| WO | WO-2018177343 | A1 * | 10/2018 ............ A23C 9/137 |
| WO | 2019135606 | A1 | 7/2019 |
| WO | 2019208668 | A1 | 10/2019 |

OTHER PUBLICATIONS

Bowen P: "Particle Size Distribution Measurement from Millimeters to Nanometers and from Rods to Platelets", Journal of Dispersion Science and Technology, Taylor and Francis Group, New York, NY, US, vol. 23, No. 5, Jan. 1, 2002 (Jan. 1, 2002), pp. 631-662.

Final Office Action for U.S. Appl. No. 17/792,843 dated Jun. 17, 2025, 34 pages.

Matsutani et al., "Resistant Starch Type 4, Cross-linked Phosphate Starch and Hydroxypropyl Distarch Phosphate Attenuate Rapid Glycemic Response in Men", Japanese Pharmacology and therapeutics, vol. 38, 371, Jan. 2010, 8 pages.

* cited by examiner

FILM-FORMING COMPOSITION CONTAINING GELLAN GUM AND STARCH, AND APPLICATION IN SOFT CAPSULE

CROSS-REFERENCE TO RELATED APPLICATIONS

This application is a U.S. national stage filing, under 35 U.S.C. § 371 (c), of International Application No. PCT/CN2020/140148, filed on Dec. 28, 2020, which claims priority to Chinese Patent Application No. CN201911394755.3, filed on Dec. 30, 2019. The entire contents of each of the aforementioned applications are incorporated herein by reference.

TECHNICAL FIELD

The present application relates to the field of food or pharmaceutical raw materials, specifically to a starch film-forming composition.

BACKGROUND OF THE INVENTION

Soft capsules are widely used in the fields of medicines, food products, cosmetics, etc. Gelatin is widely and traditionally used as a material for a soft capsule since it has excellent film-forming properties and a high mechanical strength. However, gelatin shows many drawbacks in term of qualities during use due to its own properties. For example, gelatin molecules may be oxidized on their own or cross-link with functional groups such as aldehyde groups, forming a tough and flexible water-insoluble membrane on the surface of the gelatin soft capsule, which prevents the release of drugs, resulting in unqualified soft capsules in terms of disintegration. In addition, as required by a population with a religion or vegetarians, and with the outbreak of the mad cow disease and the foot-and-mouth disease around the world, efforts are always taken to develop substitutes for gelatin and a method of their use for preparing soft capsules.

More starch film-forming compositions used for soft capsules are needed in this field.

SUMMARY OF THE INVENTION

The present disclosure is partly based on the following discovery during the long-term work of the inventors. The Chinese patent No. CN100528950C proposes a blend of different acyl gellan gums and a starch, comprising: a. a high acyl gellan gum; b. a low acyl gellan gum; c. a starch; and d. a plasticizer. The film prepared using such a blend has a high modulus and an excellent strength and elongation, and the prepared soft capsule has a desired sealability. The high acyl gellan gum and the low acyl gellan gum as gelling agents in the formulation can improve the strength and toughness of a ribbon to some extent, but the prepared soft capsules have a low transparency, and have a seam that is not tightly sealed, making the soft capsules easy to leak oil. In addition, the Japanese patent publication No. JP2007153851A proposes a composition for a soft capsule film without an animal-derived component, which is obtained by mixing water, a starch and a natural gellan gum. The European patent publication No. EP2815745A1 proposes a soft capsule and its preparation method, in which the soft capsule comprises a high acyl gellan gum, at least one starch and at least one plasticizer. The high acyl gellan gum having a soft texture and a high flexibility property can form a ribbon with a low strength and a moderate toughness together with a starch. However, the seam of a soft capsule after encapsulation is thin and the soft capsule is easy to leak oil when a low disruptive force is applied, as shown in the control examples. At present, during the preparation of soft capsules with a high acyl gellan gum and a low acyl gellan gum as the major capsule materials, there are many drawbacks, such as a high viscosity of the gel mass solution, forming a pregel easily when the gel mass solution is stored at a high temperature, forming a ribbonwith a low strength and a poor toughness, and a capsule with a thin seam thickness after encapsulation, and leaking oil easily, which causes the industrial production of soft capsules unachievable.

After a long-term research, the inventors find that the use of a gellan gum with two specific gel temperatures (with two gel temperatures, in which the first gel temperature is between 51 and 75° C., and the second gel temperature is between 40 and 50° C.), can solve the above technical problems.

The purpose of the present invention is to provide a composition with a gellan gum with two specific gel temperatures and a starch and a soft capsule prepared therefrom. It is disclosed in the art that a gel formed by a gellan gum with two gel temperatures in which the first gel temperature is between 30° C. and 40° C. and the second gel temperature is between 40° C. and 65° C. has excellent gel characteristics and texture, and can be widely used in the food field. There are two types of traditional gellan gums, a high acyl gellan gum (a natural gellan gum with a single gel temperature between 70 and 80° C.) and a low acyl gellan gum (a single gel temperature between 25 and 50° C.). After study, the inventors discover that the film prepared from a composition having a new gellan gum with two gel temperatures in which the first gel temperature ranges from 51° C. to 75° C. and the second gel temperature ranges from 40° C. to 50° C., and a starch has a suitable strength and toughness for preparing soft capsules. The prepared soft capsule has excellent properties and a good seam adhesive property for shaping, which can meet the requirements for industrial production of soft capsules. As compared to a high acyl gellan gum with a single gel temperature between 70 and 80° C. and a low acyl gellan gum with a single gel temperature between 25 and 50° C., the gellan gum, employed in the present invention, with two specific gel temperatures (the first gel temperature between 51 and 75° C. and the second gel temperature between 40 and 50° C.) improves the seam adhesive property after encapsulation and the composition of the present application has a significantly improved seam adhesive property after encapsulation as compared to a composition comprising a high acyl gellan gum or a low acyl gellan gum with a single gel temperature and a starch in the preparation of soft capsules.

The composition comprising a gellan gum with two specific gel temperatures and a starch employed in the present invention has a suitable film-forming strength and toughness. With the increase of the percentage of the gellan gum within a certain range, both the film-forming strength and toughness increase while the adhesive property for shaping decreases. The inventors determine the contents of the gellan gum and the starch suitable for preparing soft capsules by evaluating indicators of the strength and the toughness of the ribbon, and the seam adhesive property after encapsulation of the soft capsule shell.

The composition of the present invention is obviously superior to the compositions in the prior art in terms of the strength, the toughness and the seam adhesive property after encapsulation of capsule shells during the preparation of soft capsules, can fully meet the requirements for industrial production of soft capsules and can be used as an alternative in the soft capsule technology.

The invention provides a starch film-forming composition, comprising:

A. 0.5 to 6 wt % of a first gelling agent,

B. 10 to 50 wt % of starch,

C. 10 to 30 wt % of a plasticizer, and

D. 33 to 70 wt % of water, wherein the first gelling agent is gellan gum, which is characterized in having two gel temperatures, wherein the first gel temperature ranges from 51 to 75° C., and the second gel temperature ranges from 40 to 50° C.

Further, the starch film-forming composition is characterized in that:

the ratio of the weight parts of the first gelling agent to the total weight parts of the starches [(A)/(B)] is between 0.01 and 0.6, preferably between 0.02 and 0.5, or between 0.02 and 0.1.

Further, the first gelling agent is gellan gum, and preferably the ranges of the two gel temperatures are as follows: the first gel temperature between 51 and 55° C. and the second gel temperature between 40 and 50° C., or the first gel temperature between 56 and 60° C. and the second gel temperature between 40 and 50° C., or the first gel temperature between 61 and 65° C. and the second gel temperature between 40 and 50° C., or the first gel temperature between 66 and 70° C. and the second The gel temperature between 40 and 50° C., or the first gel temperature between 71 and 75° C. and the second gel temperature between 40 and 50° C.

The starch may be from natural sources such as cassava, corn, potato, wheat, waxy corn starch, or modified starches prepared by physical, chemical, enzymatic methods. The natural starch is selected from a waxy corn starch, a pea starch, a corn starch, a potato starch, and a tapioca starch. The modified starch is selected from an acid modified starch, a hydroxypropyl starch, an oxidized starch, an acetate starch, an oxidized hydroxypropyl starch, a hydroxypropyl distarch phosphate, a starch phosphate, an acetylated oxidized starch, and an acetylated distarch phosphate.

The plasticizer refers to a polyhydric alcohol, comprising one or more of glycerol, sorbitol, maltitol, erythritol, xylitol, crystalline fructose, and trehalose.

The starch film-forming composition may also comprise a second gelling agent selected from the group consisting of carrageenan, agar, sodium alginate, low methoxy pectin, high methoxy pectin, amidated pectin, high acyl gellan gum, low acyl gellan gum, pullulan, konjac glucomannan, xanthan gum, and locust bean gum.

The present invention also provides a method for preparing the starch film-forming composition, comprising: a) adding the first gelling agent to the plasticizer, stirring them homogeneously, and then adding water to the resulting mixture which is then heated at a temperature between 80 and 98° C. with stirring until the first gelling agent dissolves; b) adding the starch, and heating them at a temperature between 80 and 98° C. with stirring until the starch dissolves; and c) removing air bubbles to obtain the film-forming composition.

Further, in the preparation method, the weight ratio of the first gelling agent to the starch ranges from 0.1 to 0.6, and the b) step further comprises adding a water-soluble polysaccharide with a weight percentage between 5 and 35%; and the b) step is a step for adding the starch and the water-soluble polysaccharide, and heating them at a temperature between 80 and 98° C. with stirring until the starch and the water-soluble polysaccharide dissolve.

Further, in the preparation method, the a) step further comprises adding the second gelling agent with a weight percentage of the second gelling agent between 0.1 and 5%; and the a) step is a step for adding the first gelling agent and the second gelling agent to the plasticizer, stirring them homogeneously, and then adding the water to the resulting mixture which is then heated at a temperature between 80 and 98° C. with stirring until the first gelling agent and the second gelling agent dissolve.

The present invention provides a soft capsule prepared by the above starch film-forming composition, and the shell of the soft capsule has the follow composition:

A. 0.5 to 6 wt %, preferably 1 to 5 wt % of the first gelling agent,

B. 10 to 50 wt %, preferably 10 to 40 wt % of the starch,

C. 10 to 30 wt %, preferably 15 to 25 wt % of the plasticizer, and

D. 33 to 70 wt %, preferably 35 to 50% of water, wherein the first gelling agent is gellan gum with two gel temperatures, wherein the first gel temperature ranges from 51 to 75° C., and the second gel temperature ranges from 40 to 50° C.

Further, the present invention provides a soft capsule prepared by a starch film-forming composition, characterized in that the ratio of the weight percentage of the first gelling agent to the weight percentage of the starch [(A)/(B)] is between 0.02 and 0.6, preferably between 0.02 and 0.5, or between 0.02 and 0.1.

The starch may be selected from natural starches or modified starches, preferably a hydroxypropyl starch, an oxidized starch, an oxidized hydroxypropyl starch, a hydroxypropyl distarch phosphate, an acetylated oxidized starch, and an acetylated distarch phosphate.

The plasticizer refers to a polyhydric alcohol, comprising one or more of glycerol, sorbitol, maltitol, erythritol, xylitol, crystalline fructose, and trehalose.

The starch film-forming composition may also comprise a second gelling agent selected from a group consisting of carrageenan, agar, sodium alginate, low methoxy pectin, high methoxy pectin, amidated pectin, high acyl gellan gum, low acyl gellan gum, pullulan, konjac glucomannan, xanthan gum, and locust bean gum.

The soft capsule prepared by the starch film-forming composition may have a filling, which may comprise various animal and vegetable oils, or suspensions, emulsions or semisolids, made of various solid functional ingredients and suitable auxiliary materials for the soft capsule, or solid preparations (e.g. granules, microcapsules, powders, tablets and capsules) made of solid functional ingredients and suitable auxiliary materials.

The present invention also provides a method for preparing a soft capsule from the starch film-forming composition, comprising the following steps:

1) Gel mass preparation: a) adding the first gelling agent to the plasticizer, stirring them homogeneously, and then adding water to the resulting mixture which is then heated at a temperature between 80 and 98° C. with stirring until the first gelling agent dissolves; b) adding the starch, and heating them at a temperature between 80 and 98° C. with stirring until the starch dissolves; and c) removing air bubbles to obtain the film-forming composition.

Further, in the preparation method, the weight ratio of the first gelling agent to the starch ranges from 0.1 to 0.6, and the b) step further comprises adding a water-soluble polysaccharide with a weight percentage between 5 and 35%;

and the b) step is a step for adding the starch and the water-soluble polysaccharide, and heating them at a temperature between 80 and 98° C. with stirring until the starch and the water-soluble polysaccharide dissolve.

Further, in the preparation method, the a) step further comprises adding the second gelling agent with the weight percentage of the second gelling agent between 0.1 and 5%; and the a) step is a step for adding the first gelling agent and the second gelling agent to the plasticizer, stirring them homogeneously, and then adding the water to the resulting mixture which is then heated at a temperature between 80 and 98° C. with stirring until the first gelling agent and the second gelling agent dissolve.

2) Encapsulation and drying. The soft capsule production line is used. The gel mass solution prepared in step 1) is transported to the spreader box of the soft capsule encapsulation machine. The gel mass solution is cooled on the surface of the drum to form a ribbon. Soft capsules are obtained by encapsulation with a filling, extrusion forming with die rolls, and then drying.

The present invention provides a starch film-forming composition with desired film-forming strength and toughness, which can be used in preparation of soft capsules to obtain soft capsules with a desired adhesive property for shaping and encapsulation properties and which is free of animal-derived ingredients. The soft capsules thus are suitable for all ethnic populations in the world and can be applied globally.

The present invention provides the following contents.

In one aspect, the present invention provides a starch film-forming composition, comprising:

A. a first gelling agent;

B. starch;

C. a plasticizer; and

D. water;

wherein the first gelling agent is a gellan gum with two gel temperatures, wherein the first gel temperature ranges from 51 to 75° C., and the second gel temperature ranges from 40 to 50° C.

In one embodiment, the content of the first gelling agent ranges from 0.5 to 6 wt %, the content of the starch ranges from 10 to 50 wt %, the content of the plasticizer ranges from 10 to 30 wt %, and the content of the water ranges from 33 to 70 wt %.

In one embodiment, the weight ratio of the first gelling agent to the starch ranges from 0.02 to 0.6.

In one embodiment, the weight ratio of the first gelling agent to the starch ranges from 0.02 to 0.5, and the content of the first gelling agent ranges from 1 to 5 wt %.

In one embodiment, the weight ratio of the first gelling agent to the starch ranges from 0.1 to 0.6, and the film-forming composition further comprises 5 to 35 wt % of a water-soluble polysaccharide.

In one embodiment, the water-soluble polysaccharide is selected from a group consisting of pullulan, dextrin and maltodextrin.

In one embodiment, the starch is a modified starch; and the modified starch is selected from a group consisting of an acid modified starch, a hydroxypropyl starch, an oxidized starch, an acetate starch, an oxidized hydroxypropyl starch, a hydroxypropyl distarch phosphate, a starch phosphate, an acetylated oxidized starch, and an acetylated distarch phosphate.

In one embodiment, the starch is a natural starch, and the natural starch is selected from a group consisting of a waxy corn starch, a pea starch, a corn starch, a potato starch, and a tapioca starch.

In one embodiment, the plasticizer is selected from a group consisting of glycerol, sorbitol, maltitol, erythritol, xylitol, crystalline fructose and trehalose.

In one embodiment, the starch film-forming composition further comprises a second gelling agent, of which weight percentage ranges from 0.1 to 5%, and the second gelling agent is selected from a group consisting of carrageenan, agar, sodium alginate, low methoxy pectin, high methoxy pectin, amidated pectin, high acyl gellan gum, low acyl gellan gum, konjac glucomannan, xanthan gum and locust bean gum.

In another aspect, the present invention provides a preparation method of the starch film-forming composition according to the present invention, comprising: a) adding the first gelling agent to the plasticizer, stirring them homogeneously, and then adding water to the resulting mixture which is then heated at a temperature between 80 and 98° C. with stirring until the first gelling agent dissolves; b) adding the starch, and heating them at a temperature between 80 and 98° C. with stirring until the starch dissolves; and c) removing air bubbles to obtain the film-forming composition.

In one embodiment, the weight ratio of the first gelling agent to the starch ranges from 0.1 to 0.6, and the b) step further comprises adding a water-soluble polysaccharide with a weight percentage between 5 and 35%; and the b) step is a step for adding the starch and the water-soluble polysaccharide, and heating them at a temperature between 80 and 98° C. with stirring until the starch and the water-soluble polysaccharide dissolve.

In one embodiment, the a) step further comprises adding the second gelling agent with the weight percentage of the second gelling agent between 0.1 and 5%; and the a) step is a step for adding the first gelling agent and the second gelling agent to the plasticizer, stirring them homogeneously, and then adding the water to the resulting mixture which is then heated at a temperature between 80 and 98° C. with stirring until the first gelling agent and the second gelling agent dissolve.

In another aspect, the present invention provides a capsule shell comprising the starch film-forming composition of the present invention.

In another aspect, the present invention provides the use of the starch film-forming composition according to the present invention in a food product, a nutraceutical food product, a medicine and cosmetics.

DETAILED DESCRIPTION OF THE INVENTION

The following content is provided to further illustrate the present invention.

As used herein, "%" or "wt %" refers to weight percentage, unless otherwise indicated in the description.

The starch film-forming composition provided in the present invention comprises a first gelling agent, a starch, a plasticizer and water, wherein the first gelling agent is gellan gum with two gel temperatures, wherein the first gel temperature ranges from 51 to 75° C., and the second gel temperature ranges from 40° C. to 50° C.

As used herein, the first gelling agent has a first gel temperature between 51 and 55° C. and a second gel temperature between 40 and 50° C., or a first gel temperature between 56 and 60° C. and a second gel temperature between 40 and 50° C., or a first gel temperature between 61 and 65° C. and a second gel temperature between 40 and 50° C., or a first gel temperature 66 and 70° C. and a second gel temperature 40 and 50° C., or a first gel temperature between 71 and 75° C. and a second gel temperature between 40 and 50° C. In one embodiment, the first gelling agent is Gellaneer™ HS gellan gum. In one embodiment, the gellan gum is Gellaneer™ HS gellan gum. The gel temperatures of multiple batches of Gellaneer™ HS gellan gum are measured by the inventors and it is found that the first gel temperature ranges from 55 to 65° C. and the second gel temperature ranges from 40 to 50° C. or the first gel temperature ranges from 66 to 75° C. and the second gel temperature ranges from 40 to 50° C. The gel strength of 0.5% of gellan gum ranges from 100 to 1000 g/cm², preferably 200 to 800 g/cm², 200 to 700 g/cm², 200 to 600 g/cm², 200 to 500 g/cm², or 200 to 400 g/cm².

As used herein, the content of the first gelling agent may range from 0.5 to 6 wt %, 1 to 5 wt %, 1.5 to 3.5 wt % or 1.5 to 3 wt %. The content of the first gelling agent may be 1.0 wt %, 1.5 wt %, 2.0 wt %, 2.5 wt %, 3.0 wt %, 3.5 wt %, 4.0 wt %, 4.5 wt % or 5 wt %, or a range between these numbers.

As used herein, the content of starch may range from 2 to 50 wt %, 5 to 50 wt %, 10 to 50 wt %, 10 to 40 wt %. The content of starch may be 10 wt %, 15 wt %, 20 wt %, 25 wt %, 30 wt %, 35 wt %, 40 wt %, 45 wt % or 50 wt %, or a range between these numbers.

As used herein, the content of the water may range from 33 to 70 wt %. For example, the water content may be 33 wt %, 36 wt %, 40 wt %, 41 wt %, 44 wt %, 48 wt %, 51 wt %, 52 wt %, 53 wt %, 57 wt %, 60 wt %, 65 wt % or 70 wt %, or a range between these numbers.

As used herein, the content of the plasticizer may range from 5 to 30%, 10 to 30%, 15 to 25%, or 15 to 20%. For example, the content of the plasticizer may be 10 wt %, 15 wt %, 18 wt %, 20 wt %, 25 wt %, or 30%, or a range between these numbers.

As used herein, the plasticizer may be selected from a group consisting of glycerol, sorbitol, maltitol, erythritol, xylitol, crystalline fructose and trehalose.

As used herein, the weight ratio of the first gelling agent to the starch may range from 0.01 to 0.6, 0.02 to 0.5, 0.02 to 0.2, 0.02 to 0.1, or 0.02 to 0.08. In one embodiment, the weight ratio of the first gelling agent to the starch ranges from 0.1 to 0.6, preferably 0.1 to 0.5.

As used herein, the starch may be a modified starch. The modified starch may be selected from a group consisting of an acid modified starch, a hydroxypropyl starch, an oxidized starch, an acetate starch, an oxidized hydroxypropyl starch, a hydroxypropyl distarch phosphate, a starch phosphate, an acetylated oxidized starch, and an acetylated distarch phosphate. The starch may also be a natural starch. The natural starch can be selected from a group consisting of a waxy corn starch, a pea starch, a corn starch, a potato starch, and a tapioca starch.

As used herein, the starch film-forming composition also comprises a second gelling agent. The weight percentage of the second gelling agent may range from 0.1 to 5%. The second gelling agent may be selected from a group consisting of carrageenan, agar, sodium alginate, low methoxy pectin, high methoxy pectin, amidated pectin, high acyl gellan gum, low acyl gellan gum, konjac glucomannan, xanthan gum and locust bean gum.

In one embodiment, the weight ratio of hydroxypropyl starch to oxidized hydroxypropyl starch ranges from 1:9 to 9:1, 1:4 to 4:1 or 1:2 to 2:1. In one embodiment, the weight ratio of hydroxypropyl starch to oxidized starch ranges from 1:9 to 9:1, 1:4 to 4:1 or 1:2 to 2:1. In one embodiment, the weight ratio of hydroxypropyl distarch phosphate to oxidized hydroxypropyl starch ranges from 1:9 to 9:1, 1:4 to 4:1 or 1:2 to 2:1. In one embodiment, the weight ratio of hydroxypropyl starch to hydroxypropyl distarch phosphate ranges from 1:9 to 9:1, 1:4 to 4:1 or 1:2 to 2:1.

In one embodiment, the starch film-forming composition comprises an ingredient selected from a group consisting of pullulan, dextrin, and maltodextrin. The content may range from 5 to 35%, 15 to 30% or 20 to 30% by weight, for example 5%, 15%, 25%, 30%, or 35%.

EXAMPLES

In order to better illustrate the effects of the present invention, the following indicators of a soft capsule are used for evaluation and description.

1) Indicators of the strength and toughness of the ribbon. A texture analyzer was used and a spherical probe and puncture mode were selected. Test speed was 1.0 mm/s, and the force value (g) and the corresponding distance (mm) was recorded when the ribbon ruptures. The force applied when the ribbon ruptures represents the strength of the ribbon, and the greater the force, the better the strength of the ribbon. The distance travelled by the probe when the ribbon ruptures represents the toughness of the ribbon. The longer the distance, the better the toughness of the ribbon.

2) Indicators of the seam adhesive property after encapsulation. The samples of the examples of the present invention were taken. The capsules were cut from a position other than the seam. The contents were emptied by extrusion. Then, a ring with two seams at the middle of the capsule was cut perpendicularly to the seam. The ring was placed on a glass slide and the two seams were perpendicular to the slide glass. The thicknesses of the two seams and the capsule shell were measured under a microscope. The ratio P (%) of the thickness of the seam (which is thinnest) to that of the capsule shell was calculated.

TABLE 1

| Standards for evaluating the indicators of the ribbon strength, the ribbon toughness and the seam adhesive property after soft capsule encapsulation | | | | | | | |
|---|---|---|---|---|---|---|---|
| Evaluation | | Score | | | | | |
| Indicators | Weight | 5 points | 4 points | 3 points | 2 points | 1 point | 0 point |
| strength of the ribbon | 20% | the force applied when the ribbon ruptures ≥ 200 g | 150 g ≤ the force < 200 g | 100 g ≤ the force < 150 | 50 g ≤ the force < 100 | The force applied when the ribbon ruptures < 50 g | failure to form ribbon |

TABLE 1-continued

Standards for evaluating the indicators of the ribbon strength, the ribbon
toughness and the seam adhesive property after soft capsule encapsulation

| Evaluation | | Score | | | | | |
|---|---|---|---|---|---|---|---|
| Indicators | Weight | 5 points | 4 points | 3 points | 2 points | 1 point | 0 point |
| toughness of the ribbon | 20% | The distance travelled by the probe when the ribbon ruptures ≥ 10 mm | 8 mm ≤ the distance < 10 mm | 6 mm ≤ the distance < 8 mm | 4 mm ≤ the distance < 6 mm | the distance < 4 mm | failure to form ribbon |
| Seam adhesive property after encapsulation | 60% | P ≥ 60% | 50% ≤ P < 60% | 40% ≤ P < 50% | 30% ≤ P < 40% | 0 < P < 30% | failure to be shaped |

Comprehensive evaluation was carried out using the strength, toughness and adhesive property after encapsulation of the capsule as indicators, with a full score of 5, and each score (X) indicates:

0 point: Soft capsules cannot be formed;

0<X≤1: The shaping of the soft capsules is very poor and the soft capsules are easy to leak oil;

1<X≤2: The shaping of the soft capsules is poor and the soft capsules are easy to leak oil;

2<X3: The shaping of the soft capsules is moderate;

3<X≤4: The shaping of the soft capsules is excellent;

4<X≤5: The shaping of the soft capsules is extremely excellent.

The present invention is illustrated by using the following materials without limitation, and the details are as follows.

Gellan gum: Gellaneer™ HS, from DSM ZhongKen Biotechnology Co., Ltd. Gellan gum 1: two gel temperatures are 60° C. and 45° C. respectively, and the gel strength is 696 g/cm². Gellan gum 2: the two gel temperatures are 70° C. and 42° C. respectively, and the gel strength is 297 g/cm². Gellan gum 3: the two gel temperatures are 50° C. and 35° C. respectively, and the gel strength is 700 g/cm².

Hydroxypropyl distarch phosphate: CAS No: 53124-00-8, from Ingredion China Limited.

Hydroxypropyl starch: CAS No: 9049-76-7, from Ingredion China Limited.

Oxidized starch: CAS No: 65996-62-5, from Ingredion China Limited.

Acetylated oxidized starch: CAS No: 68187-08-6, from SMS Group (SMS)

Acetylated distarch phosphate: CAS number: 68130-14-3, from SMS Group (SMS)

Glycerin: CAS No: 56-81-5, from Wilmar (China) Oleo Co., Ltd.

Carrageenan: CAS No: 9062-07-1, purchased from Cargill, Incorporated Agar: CAS No: 9002-18-0, purchased from Luxin Food Co., Ltd.

Amidated pectin: CAS No: 9000-69-5, purchased from Azelis International Trade (Shanghai) Co., Ltd.

Low acyl gellan gum: CAS No: 71010-52-1, purchased from Azelis International Trade (Shanghai) Co., Ltd.

High Acyl Gellan Gum: CAS No: 74-79-3, from Azelis International Trade (Shanghai) Co., Ltd.

Pullulan: CAS No: 9057-02-7, from Higrand Biotech Co., Ltd

Sodium citrate: CAS No: 6132-04-3, from Guangzhou Honsea Sunshine Biotech Co., Ltd.

The method for preparing soft capsules from the starch composition, comprises:

1) Gel mass preparation. a) adding the first gelling agent (gellan gums 1-3, carrageenan, agar, amidated pectin, high acyl gellan gum or low acyl gellan gum) to glycerol, stirring them homogeneously, and then adding water to the resulting mixture which was then heated at a temperature between 80 and 98° C. with stirring until the first gelling agent dissolves; b) adding the starch, and heating them at a temperature between 80 and 98° C. with stirring until the starch dissolves; and c) removing air bubbles to obtain the film-forming composition.

In the preparation method, the weight ratio of the first gelling agent to the starch ranges from 0.1 to 0.6, and b) step may further comprise adding a water-soluble polysaccharide with a weight percentage between 5 and 35%; and the b) step is a step for adding the starch and the water-soluble polysaccharide, and heating them at a temperature between 80 and 98° C. with stirring until the starch and the water-soluble polysaccharide dissolve.

2) Encapsulation and drying. The soft capsule production line was used and the gel mass solution prepared in step 1) was transported to the spreader box of the soft capsule encapsulation machine. The gel mass solution was cooled on the surface of the drum to form a ribbon. Soft capsules were obtained by encapsulation of a filling, extrusion forming with die rolls, and then drying.

Examples 1-6

Table 2 provides the formula of the film-forming compositions used in Examples 1-6. According to the formula of Table 2, soft capsules were prepared as above and tested accordingly. The results are shown in Table 2.

TABLE 2

| Film-forming compositions and test results of Examples 1-6 | | | | | | |
| --- | --- | --- | --- | --- | --- | --- |
| components | Example 1 | Example 2 | Example 3 | Example 4 | Example 5 | Example 6 |
| Gellan gum 2 | 0.5% | 1.0% | 2.0% | 3.0% | 4.0% | 6.0% |
| Oxidized hydroxypropyl starch | 50.0% | 50.0% | 40.0% | 30.0% | 20.0% | 10.0% |
| Glycerol | 15.0% | 15.0% | 15.0% | 15.0% | 15.0% | 15.0% |
| Water | 34.5% | 34.0% | 43.0% | 52.0% | 61.0% | 69.0% |
| Weight ratio of the gellan gum to the starch | 0.01 | 0.02 | 0.05 | 0.10 | 0.20 | 0.60 |
| Strength of the ribbon | 1 | 2 | 3 | 4 | 5 | 5 |
| Toughness of the ribbon | 1 | 2 | 4 | 4 | 4 | 4 |
| Seam adhesive property after encapsulation | 2 | 3 | 5 | 5 | 2 | 1 |
| Comprehensive evaluation | 1.6 | 2.6 | 4.4 | 4.6 | 3.0 | 2.4 |

Example 1 shows that when the ratio of gellan gum to starch is less than 0.01, the ribbon is formed with low strength and toughness. Examples 2-6 show that when the ratio of gellan gum to starch is within the range of 0.02 to 0.6, the strength and toughness of the ribbon are moderate and the seam adhesive property after encapsulation is good when the ratio of gellan gum is lower than 3%; and the strength and toughness of the ribbon are better, while the seam adhesive property after encapsulation decreases when the ratio is greater than 3%.

Examples 7-15

Table 3 provides the formula of the film-forming compositions used in Examples 7-15. According to the formula of Table 3, soft capsules were prepared as above and tested accordingly. The results are shown in Table 3.

TABLE 3

| Film-forming compositions and test results of Examples 7-15 | | | | | | | | | |
| --- | --- | --- | --- | --- | --- | --- | --- | --- | --- |
| Components | Example 7 | Example 8 | Example 9 | Example 10 | Example 11 | Example 12 | Example 13 | Example 14 | Example 15 |
| Gellan gum 2 | 2.0% | 2.0% | 2.0% | / | / | 2.0% | 2.0% | 2.0% | 2.0% |
| Gellan gum 1 | / | / | / | 2.0% | / | / | / | / | / |
| Gellan gum 3 | / | / | / | / | 2.0% | / | / | / | / |
| Hydroxypropyl starch | 35.0% | / | / | / | / | / | / | / | / |
| Hydroxypropyl distarch phosphate | / | / | / | / | / | 25.0% | / | / | / |
| Acetylated oxidized starch | / | / | / | / | / | / | / | 25.0% | |
| Acetylated distarch phosphate | / | / | / | / | / | / | / | | 25.0% |
| Oxidized hydroxypropyl starch | / | / | 35.0% | 35.0% | 35.0% | / | 25.0% | / | / |
| Oxidized starch | / | 35.0% | / | / | / | / | / | / | / |
| Glycerol | 20.0% | 20.0% | 20.0% | 20.0% | 20.0% | 30.0% | 30.0% | 30.0% | 30.0% |
| Water | 43.0% | 43.0% | 43.0% | 43.0% | 43.0% | 43.0% | 43.0% | 43.0% | 43.0% |
| Weight ratio of the gellan gum to the starch | 0.06 | 0.06 | 0.06 | 0.06 | 0.06 | 0.08 | 0.08 | 0.08 | 0.08 |

TABLE 3-continued

| | Film-forming compositions and test results of Examples 7-15 | | | | | | | | |
|---|---|---|---|---|---|---|---|---|---|
| Components | Example 7 | Example 8 | Example 9 | Example 10 | Example 11 | Example 12 | Example 13 | Example 14 | Example 15 |
| Strength of the ribbon | 3 | 3 | 3 | 3 | 3 | 3 | 3 | 4 | 4 |
| Toughness of the ribbon | 4 | 4 | 4 | 4 | 4 | 4 | 4 | 4 | 4 |
| Seam adhesive property after encapsulation | 4 | 4 | 5 | 4 | 0 | 4 | 4 | 3 | 2 |
| Comprehensive evaluation | 3.8 | 3.8 | 4.4 | 3.8 | 1.4 | 3.8 | 3.8 | 3.4 | 2.8 |

Examples 7-9 show that when the ratio of gellan gum to starch is 0.06, the strength and toughness of the ribbon are moderate, but the seam adhesive property after encapsulation when oxidized hydroxypropyl starch is used is better than that when hydroxypropyl starch or oxidized starch is used. Examples 9-11 shows that when the ratio of gellan gum and starch is 0.06, Gellan gum 1 or Gellan gum 2 but not Gellan gum 3 can be prepared to soft capsules together with oxidized hydroxypropyl starch. Thus, a gellan gum with different double gel temperatures has a greater impact on the adhesive property for encapsulation. The results cannot be deduced reasonably. Examples 12-15 show that when the ratio of gellan gum and starch is 0.08, the strength and toughness of the ribbon are moderate, but the seam adhesive property after encapsulation when hydroxypropyl oxide starch or hydroxypropyl distarch phosphate is used is better than that when acetylated oxidized starch or acetylated distarch phosphate is used.

Examples 16-23

Table 4 provides the formula of the film-forming compositions used in Examples 16-23. According to the formula of Table 4, soft capsules were prepared as above and tested accordingly. The results are shown in Table 4.

TABLE 4

| | Film-forming compositions and test results of Examples 16-23 | | | | | | | |
|---|---|---|---|---|---|---|---|---|
| Components | Example 16 | Example 17 | Example 18 | Example 19 | Example 20 | Example 21 | Example 22 | Example 23 |
| Gellan gum 2 | 2.0% | 2.0% | 2.0% | 2.0% | 2.0% | 2.0% | 2.0% | 2.0% |
| Hydroxypropyl starch | 31.5% | 3.5% | 28.0% | 7.0% | / | / | 15.0% | 10.0% |
| Hydroxypropyl distarch phosphate | / | / | / | / | 28.0% | 7.0% | 10.0% | 15.0% |
| Oxidized hydroxypropyl starch | 3.5% | 31.5% | / | / | 7.0% | 28.0% | / | / |
| Oxidized starch | / | / | 7.0% | 28.0% | / | / | / | / |
| Glycerol | 20.0% | 20.0% | 20.0% | 20.0% | 20.0% | 20.0% | 30.0% | 30.0% |
| Water | 43.0% | 43.0% | 43.0% | 43.0% | 43.0% | 43.0% | 43.0% | 43.0% |
| Weight ratio of the gellan gum to the starch | 0.06 | 0.06 | 0.06 | 0.06 | 0.06 | 0.06 | 0.08 | 0.08 |
| Strength of the ribbon | 3 | 3 | 3 | 3 | 3 | 3 | 3 | 3 |
| Toughness of the ribbon | 4 | 4 | 3 | 4 | 4 | 4 | 4 | 4 |
| Seam adhesive property after encapsulation | 3 | 5 | 3 | 4 | 4 | 5 | 3 | 4 |
| Comprehensive evaluation | 3.2 | 4.4 | 3.0 | 3.8 | 3.8 | 4.4 | 3.2 | 3.8 |

Examples 16-17 show that when the ratio of gellan gum to starch is 0.06, the seam adhesive property after encapsulation is improved with the increase of content of oxidized hydroxypropyl starch in the composition comprising hydroxypropyl starch and oxidized hydroxypropyl starch. Examples 18-19 show that when the ratio of gellan gum to starch is 0.06, the seam adhesive property after encapsulation is improved with the increase of content of oxidized starch in the composition comprising hydroxypropyl starch and oxidized starch. Examples 20-21 show that when the ratio of gellan gum to starch is 0.06, the seam adhesive property after encapsulation is improved with the increase of content of oxidized hydroxypropyl starch in the composition comprising oxidized hydroxypropyl starch and hydroxypropyl distarch phosphate. Examples 22-23 show that when the ratio of gellan gum to starch is 0.08, the seam adhesive property after encapsulation is improved with the increase of content of hydroxypropyl distarch phosphate in the composition comprising hydroxypropyl starch and hydroxypropyl distarch phosphate.

Examples 24-27

Table 5 provides the formula of the film forming compositions used in Examples 24-27. According to the formula in Table 5, soft capsules were prepared as above and tested accordingly. The results are shown in Table 5.

TABLE 5

Film-forming compositions and test results of Examples 24-27

| Components | Example 24 | Example 25 | Example 26 | Example 27 |
|---|---|---|---|---|
| Gellan gum 2 | 1.0% | 2.0% | 5.0% | 6.0% |
| Hydroxypropyl distarch phosphate | 10.0% | 10.0% | 10.0% | 10.0% |
| Pullulan | 35.0% | 30.0% | 15.0% | 5.0% |
| Glycerol | 15.0% | 15.0% | 15.0% | 10.0% |
| Water | 39.0% | 43.0% | 55.0% | 69.0% |
| Weight ratio of the gellan gum to the starch | 0.10 | 0.20 | 0.50 | 0.60 |
| Strength of the ribbon | 2 | 3 | 5 | 5 |
| Toughness of the ribbon | 2 | 3 | 4 | 4 |
| Seam adhesive property after encapsulation | 3 | 4 | 2 | 2 |
| Comprehensive evaluation | 2.6 | 3.6 | 3.0 | 3.0 |

Examples 24-27 show that when the ratio of gellan gum to starch is more than 0.1, and when ingredients with low viscosity such as pullulan, or ingredients with high-viscosity (e.g. dextrin, maltodextrin) are used in the composition, not only the strength and toughness of the ribbon but also the seam adhesive property after encapsulation can be improved. It is proved that the technical effects of the composition of the present application having the gellan gum and the starch within a specific range cannot be simply deduced reasonably.

Examples 28-30

Table 6 provides the formula of the film forming compositions used in Examples 28-30. According to the formula in Table 6, soft capsules were prepared as above and tested accordingly. The results are shown in Table 6.

TABLE 6

Film-forming compositions and test results of Examples 28-30

| Components | Example 28 | Example 29 | Example 30 |
|---|---|---|---|
| Gellan gum 2 | 2% | 2.0% | 2.0% |
| Oxidized hydroxypropyl starch | 35.0% | 35.0% | 35.0% |
| Carrageenan | 3.0% | / | / |
| Agar | / | 1.0% | / |
| Amidated pectin | / | / | 1.0% |
| Glycerol | 20.0% | 20.0% | 20.0% |
| Water | 40.0% | 42.0% | 42.0% |
| Weight ratio of the gellan gum to the starch | 0.06 | 0.06 | 0.06 |
| Strength of the ribbon | 5 | 4 | 4 |
| Toughness of the ribbon | 5 | 4 | 4 |
| Seam adhesive property after encapsulation | 4 | 4 | 4 |
| Comprehensive evaluation | 4.2 | 3.4 | 3.2 |

Examples 28-30 show that the second gelling agent is helpful in improving the strength of ribbon from the film-forming composition comprising the gellan gum and starch. Also, the carrageenan is helpful in improving the toughness of the ribbon.

Control Examples 1-4

Table 7 provides the formula of the film-forming compositions used in Control Examples 1-4. According to the formula in Table 7, soft capsules were prepared as above and tested accordingly. The results are shown in Table 7.

TABLE 7

Film-forming compositions and test results of Control Examples 1-4

| Components | Control Example 1 | Control Example 2 | Control Example 3 | Control Example 4 |
|---|---|---|---|---|
| High acyl gellan gum | 2.0% | / | 3.5% | 3.5% |
| Low acyl gellan gum | / | 2.0% | 0.24% | / |
| Hydroxypropyl starch | 35.0% | 35.0% | 33.16% | 34.12% |
| Glycerol | 20.0% | 20.0% | 15.0% | 16.0% |
| Sodium citrate | / | / | 0.1% | 0.1% |
| Water | 43.0% | 43% | 48.0% | 46.28% |
| Strength of the ribbon | 2 | 5 | 4 | 3 |
| Toughness of the ribbon | 3 | 1 | 3 | 4 |
| Seam adhesive property after encapsulation | 1 | 0 | 1 | 1 |
| Comprehensive evaluation | 1.2 | 1.2 | 2.0 | 2.0 |

The high acyl gellan gum and the low acyl gellan gum are used in Control Example 1 and Control Example 2 respectively, and the contents of the components are the same as those of Example 7. The strength of the ribbon in Control Example 1 in which the high acyl gellan gum is used is weak and the seam adhesive property after encapsulation is very poor, making the capsule easy to leak oil. The strength of the ribbon in Control Example 2 in which the low acyl gellan gum is used is high, but the toughness and the seam adhesive property after encapsulation are low. Thus, soft capsules cannot be prepared from the composition of Control Example 2. Control Example 3 and Control Example 4 are examples of compositions comprising the high acyl gellan gum and the low acyl gellan gum (see European patent publication No. EP2815745A1, which is incorporated herein by reference, for example, Example 2 Table 2 Batch No. 1, Batch No. 5, at page 6), showing that the technical effect of the composition comprising the gellan gum and starch of the present invention is improved as compared to those in the prior art.

The composition having the gellan gum with two specific gel temperatures and a starch of the present invention has high film-forming strength and toughness, both of which increase with the increase of the content of the gellan gum within a particular range. However, the seam adhesive property after encapsulation decreases with the increase of the content of the gellan gum within a particular range. The composition of the present invention having the gellan gum with two specific gel temperatures and a starch can be used to prepare soft capsules which is obviously superior to those in the prior art in terms of the ribbon strength, ribbon toughness, and seam adhesive property after encapsulation. The composition of the present application can fully meet the requirements for industrial production of soft capsules and can be used as an alternative in soft capsule technology.

The above examples are preferred embodiments of the present invention, but the present invention are not limited to the above examples, and any other changes, modifications, substitutions, combinations, simplification made without departing from the spirit and principle of the present invention should be deemed as being equivalent to the present application, and are all included in the claimed scope of the present invention.

The invention claimed is:

1. A starch film-forming composition, comprising:
   (a) a first gelling agent;
   (b) starch;
   (c) a plasticizer; and
   (d) water;
   wherein the first gelling agent is a gellan gum with two gel temperatures, wherein the first gel temperature is 70° C., and the second gel temperature is 42° C.,
   wherein a weight ratio of the first gelling agent to the starch ranges from 0.05 to 0.1, and the starch is selected from the group consisting of:
   (i) a mixture of hydroxypropyl starch and an oxidized hydroxypropyl starch, wherein a weight ratio between the hydroxypropyl starch and the oxidized hydroxypropyl starch is 1:9;
   (ii) a mixture of a hydroxypropyl starch and an oxidized starch, wherein a weight ratio between the hydroxypropyl starch and the oxidized starch is 1:4; and
   (iii) a mixture of a hydroxypropyl starch and a hydroxypropyl distarch phosphate, wherein a weight ratio between the hydroxypropyl starch and the hydroxypropyl distarch phosphate is 2:1 to 9:1.

2. The starch film-forming composition according to claim 1, wherein the content of the first gelling agent ranges from 2 to 6 wt %, the total content of the starch ranges from 25 to 50 wt %, the content of the plasticizer ranges from 10 to 30 wt %, and the content of the water ranges from 33 to 70 wt %.

3. The starch film-forming composition according to claim 2, wherein the film-forming composition further comprises 5 to 35 wt % of a water-soluble polysaccharide.

4. The starch film-forming composition according to claim 3, wherein the water-soluble polysaccharide is selected from a group consisting of pullulan, dextrin and maltodextrin.

5. The starch film-forming composition according to claim 1, wherein the plasticizer is selected from the group consisting of glycerol, sorbitol, maltitol, erythritol, xylitol, crystalline fructose and trehalose.

6. The starch film-forming composition according to claim 5, further comprising a second gelling agent, wherein the weight percentage of the second gelling agent ranges from 0.1 to 5 wt %, and the second gelling agent is selected from a group consisting of carrageenan, agar, sodium alginate, low methoxy pectin, high methoxy pectin, amidated pectin, high acyl gellan gum, low acyl gellan gum, konjac glucomannan, xanthan gum and locust bean gum.

7. A method for preparing the starch film-forming composition according to claim 2, comprising: a) adding the first gelling agent to the plasticizer, stirring homogeneously to form a mixture, and then adding water to the mixture which is then heated at a temperature between 80° C. and 98° C. with stirring until the first gelling agent dissolves; b) adding the starch, and heating at a temperature between 80° C. and 98° C. with stirring until the starch dissolves; and c) removing air bubbles to obtain the film-forming composition.

8. The preparation method according to claim 7, wherein the b) step further comprises adding a water-soluble polysaccharide with a weight percentage between 5 and 35 wt %; and the b) step is a step for adding the starch and the water-soluble polysaccharide, and heating at a temperature between 80° C. and 98° C. with stirring until the starch and the water-soluble polysaccharide dissolves.

9. The preparation method according to claim 7, wherein the a) step further comprises adding a second gelling agent with the weight percentage of the second gelling agent between 0.1 and 5 wt %; and the a) step is a step for adding the first gelling agent and the second gelling agent to the plasticizer, stirring homogeneously to form the mixture, and then adding the water to the mixture which is then heated at a temperature between 80° C. and 98° C. with stirring until the first gelling agent and the second gelling agent dissolves.

10. A capsule shell comprising the starch film-forming composition of claim 1.

11. The preparation method according to claim 8, wherein the a) step further comprises adding a second gelling agent with the weight percentage of the second gelling agent between 0.1 and 5 wt %; and the a) step is a step for adding the first gelling agent and the second gelling agent to the plasticizer, stirring homogeneously to form the mixture, and then adding the water to the mixture which is then heated at a temperature between 80° C. and 98° C. with stirring until the first gelling agent and the second gelling agent dissolves.

12. The starch film-forming composition according to claim 6, wherein the weight percentage of the second gelling agent ranges from 1 to 3 wt %, and the second gelling agent is selected from a group consisting of carrageenan, agar, and amidated pectin.

13. The starch film-forming composition according to claim 2, wherein the content of the first gelling agent ranges from 2 to 3 wt %, the total content of the starch ranges from 35 to 40 wt %, the content of the plasticizer ranges from 10 to 30 wt %, and the content of the water ranges from 33 to 60 wt %.

14. A capsule shell comprising the starch film-forming composition of claim 6.

* * * * *